(12) United States Patent
Zhang et al.

(10) Patent No.: US 12,344,575 B1
(45) Date of Patent: Jul. 1, 2025

(54) PROCESS FOR REDUCING BY-PRODUCTS IN BISPHENOL A REACTION SYSTEM

(71) Applicant: TIANJIN UNIVERSITY, Tianjin (CN)

(72) Inventors: Minhua Zhang, Tianjin (CN); Yingzhe Yu, Tianjin (CN); Hao Gong, Tianjin (CN); He Dong, Tianjin (CN); Sheng Wang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/968,658

(22) Filed: Dec. 4, 2024

(30) Foreign Application Priority Data

Apr. 11, 2024 (CN) .......................... 202410437975.4

(51) Int. Cl.
*C07C 37/20* (2006.01)
*B01J 21/00* (2006.01)
*B01J 31/00* (2006.01)

(52) U.S. Cl.
CPC .................... *C07C 37/20* (2013.01)

(58) Field of Classification Search
CPC ............ C07C 37/20; B01J 21/00; B01J 31/00
See application file for complete search history.

(56) References Cited

U.S. PATENT DOCUMENTS

| 6,960,697 B2 * | 11/2005 | O'Young | C07C 37/20 |
| | | | 568/728 |
| 10,604,465 B2 * | 3/2020 | Eijsbouts | C07C 37/20 |
| 11,760,710 B2 * | 9/2023 | Palmer | C07C 37/86 |
| | | | 568/724 |
| 2023/0340196 A1 * | 10/2023 | Uchiyama | C08G 64/06 |
| 2024/0308944 A1 * | 9/2024 | Daliparthi | C07C 37/84 |

FOREIGN PATENT DOCUMENTS

| CN | 1200105 A | 11/1998 |
| CN | 112409139 A | 2/2021 |
| IN | 2008DN02701 A | 3/2009 |

* cited by examiner

*Primary Examiner* — Sikarl A Witherspoon (57) ABSTRACT

The present disclosure provides a process for reducing by-products in a bisphenol A reaction system. The process includes the following steps: conveying mother liquor produced after reaction, concentration, crystallization and separation of phenol and acetone to a mother liquor recovery system; subjecting the mother liquor obtained from the mother liquor recovery system and a sulfo-containing metal organic framework catalyst to contact for an isomerization reaction; and conveying a product obtained from the isomerization reaction to the mother liquor recovery system, to obtain bisphenol A after crystallization and dephenolization.

5 Claims, 10 Drawing Sheets

PROCESS FOR REDUCING BY-PRODUCTS IN BISPHENOL A REACTION SYSTEM

CROSS-REFERENCE TO RELATED APPLICATION

This application claims priority from the Chinese patent application 2024104379754 filed Apr. 11, 2024, the content of which is incorporated herein in the entirety by reference.

TECHNICAL FIELD

The present disclosure relates to a process for reducing by-products in a bisphenol A reaction system, in particular to a process for preparing bisphenol A by catalytic isomerization of by-products 2,4-BPA, triphenol and chroman in a bisphenol A reaction system.

BACKGROUND ART

Bisphenol A (BPA), with a chemical name of 2,2-bis(4-hydroxyphenyl)propane, is a widely-used organic chemical raw material prepared through condensation between phenol and acetone under an action of a catalyst, which is mainly used for producing various high polymer materials such as polycarbonate and epoxy resin.

2,4-bisphenol A (2,4-BPA for short) will be by-produced in a bisphenol A reaction, and meanwhile, p-isopropenylphenol produced through condensation between the phenol and the acetone can continue to react with a main product bisphenol A to produce 4-(2,2,4-trimethylbenzopyran-4-yl) phenol (abbreviated as triphenol). In addition, the raw phenol contains a small amount of isopropylidene acetone and isopropylidene acetone produced by the acetone itself under acidic catalysis conditions, and 2-2-4-trimethyl-4-(4'-hydroxyphenyl)-chroman and 1,1,3-trimethyl-1-(4'-hydroxyphenyl)indan-6-ol (abbreviated as chroman) are produced by way of the condensation of the isopropylidene acetone and the phenol. The by-products in the above bisphenol A reaction affect purity and chromaticity of the bisphenol A product, thereby affecting product quality and downstream application. Therefore, the treatment of crystallization mother liquor becomes a key step to ensure final product quality and raw materials.

In order to solve the above problems, more bisphenol A products are obtained by carrying out an isomerization reaction on the bisphenol A by-products. Chinese patent CN 200880004965.0 disclosed a method for preparing bisphenol A from phenol and acetone through catalytic condensation reaction in the presence of promoted sulfonated ion exchange resin, and concentrated crystallization liquor streams of the bisphenol A are isomerized in the presence of a macroporous sulfonated ion exchange resin catalyst. Chinese patent CN 201380033378.5 disclosed a method for preparing bisphenol A. According to the method, a mixture obtained after a reaction between phenol and acetone is concentrated, crystallized and subjected to solid-liquid separation to obtain mother liquor, one part of obtained mother liquor is isomerized, and then crystallization and solid-liquid separation are carried out so as to obtain bisphenol A. Chinese patent CN 202080047470.7 disclosed an isomerization method for a product obtained from preparation of bisphenol A through a condensation reaction between ketone and phenol. The product and ion exchange resin containing sulfo groups are isomerized under aqueous conditions, and bisphenol is obtained after separation.

At present, catalysts for catalyzing an isomerization reaction of bisphenol A by-products 2,4-BPA in the industry are acidic ion exchange resins, however, these catalysts exhibit relatively poor catalytic selectivity and low catalytic stability, and are prone to blockage of pore canals and deactivation due to coking. This is mainly due to the fact that molecular sizes of the bisphenol A by-products are large, which requires larger reaction space, and the resin is limited by crosslinking degree and swelling, resulting in poor pore size modulation, which is not conducive to mass transfer diffusion of the by-products during a catalytic reaction. Meanwhile, sulfo groups and sulfydryl exerting catalytic isomerization activity in the isomerization reaction are likely to run off from the resin, resulting in a decrease in catalytic performance as well as corrosion of equipment, thereby affecting subsequent separation and product quality.

In conclusion, in an existing reaction process for catalytically synthesizing bisphenol A by utilizing resin, an appropriate process solution for obtaining the bisphenol A through isomerization conversion of by-products in a reaction is not considered, and especially for the post-reaction crystallized mother liquor, it lacks an approach to maximize the collection and enrichment of the by-products, and no appropriate isomerization treatment operation scheme is considered for multi-component and macromolecular by-products. Therefore, it is urgent to develop a process for efficiently reducing by-products in a bisphenol A reaction system, and a catalyst, suitable for an isomerization reaction of the by-products in the bisphenol A reaction system, obtained through a preparation method achieving adjustable pore canal structures and controllable acid sites.

Therefore, the present disclosure develops a novel isomerization treatment method and an appropriate isomerization catalyst matched therewith to solve the problems such as poor enrichment of by-products and poor isomerization reaction activity in a catalytic isomerization treatment process of the bisphenol A by-products. Main innovations are as follows: in the isomerization treatment method, bisphenol A-containing by-products produced after reaction, concentration, crystallization, and separation of phenol and acetone are collected, and mother liquor rich in the bisphenol A by-products is obtained and conveyed to an isomerization reactor; and a sulfo-containing metal organic framework catalyst with an adjustable sulfonic acid amount and sulfydryl quantity and a suitable bisphenol A macromolecular by-product reaction is used for catalyzing bisphenol A isomerization by-products, thereby achieving a high conversion rate of the bisphenol A by-products and a high yield of the bisphenol A.

SUMMARY

The present disclosure aims to provide a process for reducing by-products in a bisphenol A reaction system. One part of mother liquor produced after reaction, concentration, crystallization, and separation of phenol and acetone is respectively conveyed to a cracking rearrangement reactor and an isomerization reactor, then the mother liquor and a sulfo-containing metal organic framework catalyst are in contact for an isomerization reaction, and an obtained product is crystallized and separated, to obtain bisphenol A. The by-products in the bisphenol A reaction system are treated through the process, the bisphenol A by-products are efficiently converted into bisphenol A, with a high conversion rate of the bisphenol A by-products, and the obtained product bisphenol A has a high yield.

Isomerization reaction equation is as follows:

In order to achieve the objectives of the present disclosure, the technical solution of the present disclosure is as follows.

A process for reducing by-products in a bisphenol A reaction system, mother liquor produced after reaction, concentration, crystallization, and separation of phenol and acetone is respectively sent to a cracking rearrangement reactor and an isomerization reactor, then the mother liquor is contacted with a sulfo-containing metal organic framework catalyst for an isomerization reaction, and an obtained product is crystallized and separated to obtain bisphenol A.

A process for reducing by-products in a bisphenol A reaction system, includes the following steps:
(a) conveying mother liquor to a mother liquor recovery system, wherein the mother liquor is produced by reaction, concentration, crystallization and separation of phenol and acetone;
(b) subjecting the mother liquor obtained from the mother liquor recovery system to contact with a sulfo-containing metal organic framework catalyst for an isomerization reaction; and
(c) conveying a product obtained from the isomerization reaction to the mother liquor recovery system, performing crystallization and dephenolization to obtain bisphenol A.

The step (a) comprises: the phenol and the acetone are synthesized in a bisphenol A reactor to obtain bisphenol A, and bisphenol A reaction liquor from an outlet of the bisphenol A reactor is conveyed to a concentration tower for concentration; light components obtained from a tower top of the concentration tower are recovered by a solvent recovery system to obtain the phenol and the acetone, and the phenol and the acetone are conveyed to the bisphenol A reactor; concentrated reaction liquor obtained from a tower kettle of the concentration tower is conveyed to a crystallization reactor for crystallization with the phenol, to obtain a bisphenol A adduct and reactor crystallization mother liquor; the bisphenol A adduct is conveyed to a dephenolization reactor to remove the phenol therefrom, to obtain a bisphenol A product, the removed phenol is conveyed to the mother liquor recovery system; the reactor crystallization mother liquor is conveyed to the mother liquor recovery system for mother liquor recovery; and the phenol recovered from the mother liquor recovery system is conveyed to the bisphenol A reactor, and the bisphenol A adduct recovered from the mother liquor recovery system is conveyed to the crystallization reactor.

The step (b) comprises: one part of recovery system crystallization mother liquor obtained after recovery of the phenol and the bisphenol A adduct from the mother liquor recovery system is conveyed to an isomerization reactor filled with the sulfo-containing metal organic framework catalyst for an isomerization reaction; the other part of the recovery system crystallization mother liquor is conveyed to a cracking rearrangement reactor for a cracking rearrangement reaction, and an obtained cracking rearrangement product is conveyed to the mother liquor recovery system; wherein, in the isomerization reaction, the catalyst is contacted with the mother liquor in a fixed-bed reaction, the reaction temperature ranging from 50° C. to 90° C., the reaction pressure ranging from 0.1 MPaA to 1.0 MPaA, and a liquid hourly space velocity ranging from 0.1 $h^{-1}$ to 10 $h^{-1}$.

The step (c) comprises: an isomerization product from an outlet of the isomerization reactor is conveyed to the mother liquor recovery system for crystallization with the phenol through the crystallization reactor, to obtain the bisphenol A adduct, and the bisphenol A adduct enters the dephenolization reactor to remove the phenol therefrom, so as to obtain the bisphenol A product.

The recovery system crystallization mother liquor in the step (a) is a mixture containing 2,4-BPA, the phenol, and the bisphenol A adduct; and the isomerization reactor is a fixed-bed reactor.

The sulfo-containing metal organic framework catalyst in the step (b) is formed by connecting metal ions or metal clusters and organic ligands through coordination bonds, and metal contained therein is one or a combination of Al, Mg, Ti, Cr, Fe, Cu, Zn, Zr, Ce, and Hf; the organic ligands contained therein are one or a combination of terephthalic acid, trimesic acid and imidazole compounds; a pore size of the catalyst ranges from 0.5 nm to 10 nm, a specific surface area ranges from 100 $m^2/g$ to 5,000 $m^2/g$, and an amount of sulfo groups ranges from 0.01 mmol/g to 8.0 mmol/g.

The sulfo-containing metal organic framework catalyst is prepared by any one of the preparation method of one-step synthesis, post-synthesis acid treatment, or post-synthesis oxidation treatment.

The one-step synthesis preparation method of the sulfo-containing metal organic framework catalyst comprises the following steps: dissolving and stirring metal precursor salts and sulfo-containing organic ligands in N,N-dimethylamide and then static crystallizing the solution in a crystallization kettle at 140° C. to 160° C. for 24 hours to 36 hours, and subjecting an obtained crystallized product to filtering, washing with methanol and the N,N-dimethylamide, and drying, to obtain a sulfo-containing metal organic framework material; wherein the metal precursor salt is one or a combination of oxides, nitrates, chloride salts, and acetylacetone salts of one or a combination of Al, Mg, Ti, Cr, Fe, Cu, Zn, Zr, Ce, and Hf; and the sulfo-containing organic ligands are one or a combination of benzoic acid with sulfo groups, terephthalic acid with sulfo groups, trimesic acid with sulfo groups, and imidazole compounds with sulfo groups.

The post-synthesis acid treatment preparation method of the sulfo-containing metal organic framework catalyst comprises the following steps: dissolving and stirring metal precursor salts and organic ligands in N,N-dimethylamide, and then static crystallizing the solution in a crystallization kettle at 120° C. to 160° C. for 24 hours to 48 hours, and subjecting a crystallized product obtained in the crystallization kettle to filtering, washing with methanol and the N,N-dimethylamide, and drying, to obtain a metal organic framework precursor; and putting the obtained metal organic framework precursor into a polytetrafluoroethylene-lined reaction kettle, adding acidic liquor, sulfonating at 100° C. to 180° C. for 24 hours, and subjecting an obtained product to filtering, washing, and drying, to obtain a sulfo-containing metal organic framework material; wherein the metal precursor salt is one or a combination of oxides, nitrates, chloride salts, and acetylacetonates of one or a combination of Al, Mg, Ti, Cr, Fe, Cu, Zn, Zr, Ce, and Hf; the organic ligands are one or a combination of terephthalic acid not containing amino groups or containing amino groups, trimesic acid not containing amino groups or containing amino groups, and imidazole compounds not containing amino groups or containing amino groups; the metal organic framework material precursor is formed by connecting metal ions or metal clusters and organic ligands through coordination bonds; and the acidic liquor is one or a combination of sulfuric acid, chlorosulfonic acid, and 1,3-propanesultone.

The post-synthesis oxidation treatment preparation method of the sulfo-containing metal organic framework catalyst comprises the following steps: dissolving and stirring metal precursor salts and sulfydryl-containing organic ligands in N,N-dimethylamide, and then static crystallizing the solution in a crystallization kettle at 110° C. to 140° C. for 24 hours to 48 hours, and subjecting a crystallized product obtained in the crystallization kettle to filtering, washing with ethanol, and drying, to obtain a metal organic framework precursor; and putting the obtained metal organic framework precursor into a polytetrafluoroethylene-lined reaction kettle, adding oxidative liquor, oxidizing at 50° C. to 60° C. for 2 hours to 6 hours, and subjecting an obtained product to filtering, washing, and drying, to obtain a sulfo-containing metal organic framework material; wherein the metal precursor salt is one or a combination of oxides, nitrates, chloride salts, and acetylacetonates of one or a combination of Al, Mg, Ti, Cr, Fe, Cu, Zn, Zr, Ce, and Hf; the organic ligands are one or a combination of terephthalic acid containing alkyl sulfydryl or amino sulfydryl, trimesic acid containing alkyl sulfydryl or amino sulfydryl, and imidazole compounds containing alkyl sulfydryl or amino sulfydryl; and the metal organic framework material precursor is formed by connecting metal ions or metal clusters and organic ligands through coordination bonds; the oxidative liquor is hydrogen peroxide.

The present disclosure has the following advantages and beneficial effects:

(1) The novel process for reducing the by-products in the bisphenol A reaction system involved in the present disclosure is characterized in that a process for the isomerization reaction of the bisphenol A by-products is invented, the bisphenol A by-products can be efficiently converted into the bisphenol A, and a catalytic conversion rate of bisphenol A by-products 2,4-BPA is high, which can reach 28% to 55%; and bisphenol A selectivity is high, which can reach 80% to 90%.

(2) The novel process for reducing the by-products in the bisphenol A reaction system involved in the present disclosure is characterized in that the catalyst for the isomerization reaction of the bisphenol A by-products is invented, an amount of sulfonic acid and a pore size of the catalyst can be adjusted, and a catalytic conversion rate of the bisphenol A by-products is high, which can reach 28% to 55%; and bisphenol A selectivity is high, which can reach 80% to 90%.

(3) The novel process for reducing the by-products in the bisphenol A reaction system involved in the present disclosure is characterized in that the catalyst for the isomerization reaction of the bisphenol A by-products is invented, achieving a decrease in acidic functional groups such as sulfo groups and sulfydryl running off from the catalyst and alleviation of corrosion to equipment.

BRIEF DESCRIPTION OF THE DRAWINGS

Wherein, 101: bisphenol A reactor, 102: concentration tower, 103: crystallization reactor, 104: dephenolization reactor, 105: solvent recovery system, 106: mother liquor recovery system, 107: isomerization reactor, and 108: cracking rearrangement reactor.

DETAILED DESCRIPTION OF THE PRESENT DISCLOSURE

The present disclosure is further described in detail below with reference to the accompanying drawings and specific examples. The following examples are merely descriptive and not restrictive, and do not limit the scope of protection of the present disclosure.

The specific implementation process of the method of the present application is described below with specific examples.

Example 1

Figure 1:
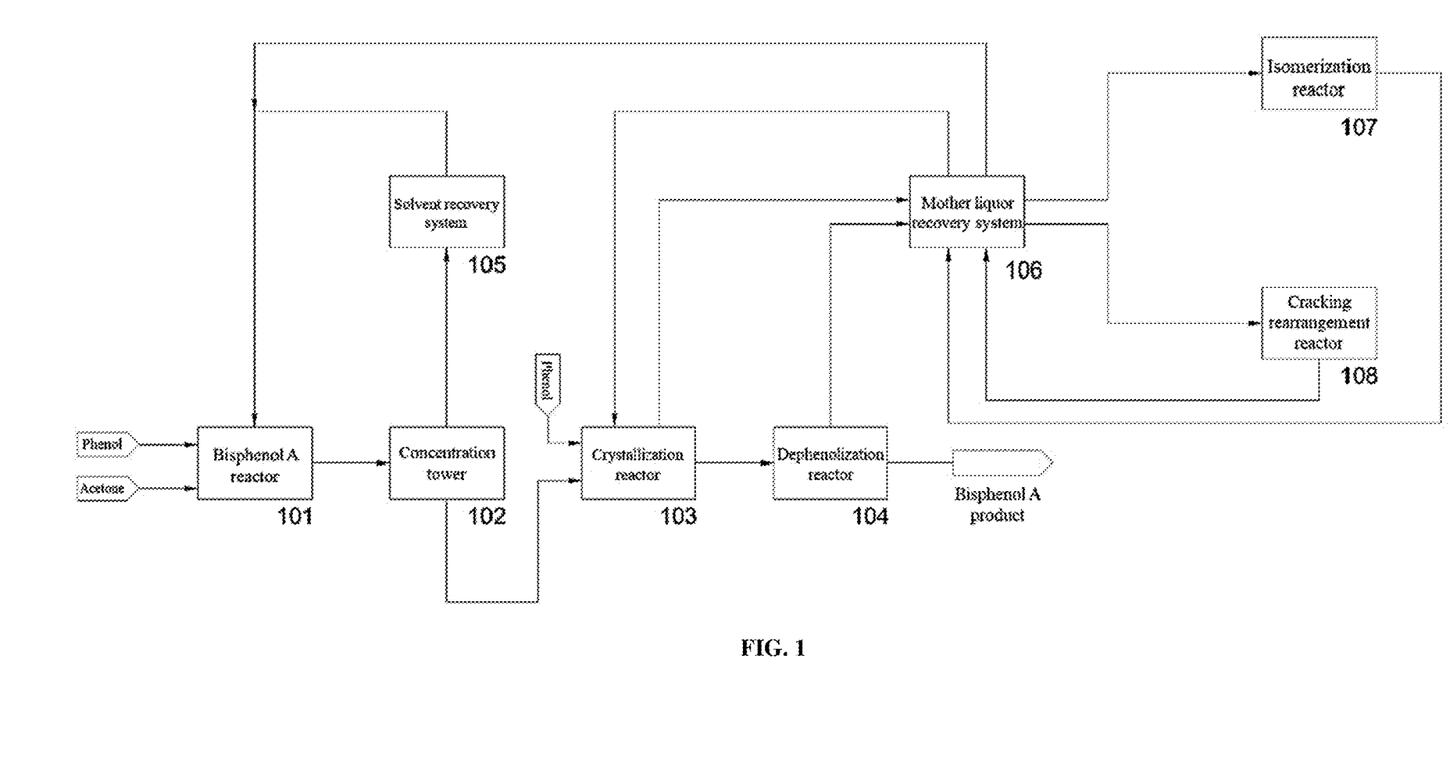
FIG. 1 is a simplified flowchart of a process for reducing by-products in a bisphenol A reaction system according to the present disclosure.

In this example, a bisphenol A preparation process is as follows (shown in FIG. 1):

(a) phenol and acetone are synthesized in a bisphenol A reactor 101, to obtain bisphenol A, and bisphenol A reaction liquor from an outlet of the bisphenol A reactor 101 is conveyed to a concentration tower 102 for concentration; light components obtained from a tower top of the concentration tower 102 are recovered by a solvent recovery system, to obtain the phenol and the acetone, and the phenol and the acetone are conveyed to the bisphenol A reactor 101; concentrated reaction liquor obtained from a tower kettle of the concentration tower 102 is conveyed to a crystallization reactor 103 for crystallization with the phenol, to obtain a bisphenol A adduct and reactor crystallization mother liquor; the bisphenol A adduct is conveyed to a dephenolization reactor 104 to remove the phenol therefrom, to obtain a bisphenol A product, the removed phenol is conveyed to the mother liquor recovery system 106; the reactor crystallization mother liquor is conveyed to the mother liquor recovery system 106 for mother liquor recovery; and the phenol recovered from the mother liquor recovery system 106 is conveyed to the bisphenol A reactor 101, and the bisphenol A adduct recovered from the mother liquor recovery system 106 is conveyed to the crystallization reactor 103;

(b) one part of recovery system crystallization mother liquor obtained after recovery of the phenol and the bisphenol A adduct from the mother liquor recovery system 106 is conveyed to an isomerization reactor 107 filled with a sulfo-containing metal organic framework catalyst for an isomerization reaction; the other part of the recovery system crystallization mother liquor obtained after recovery of the phenol and the bisphenol A adduct from the mother liquor recovery system 106 is conveyed to a cracking rearrangement reactor 108 for a cracking rearrangement reaction, and an obtained cracking rearrangement product is conveyed to the mother liquor recovery system 106; and (c) an isomerization product from an outlet of the isomerization reactor 107 is conveyed to the mother liquor recovery system 106.

Figure 2:
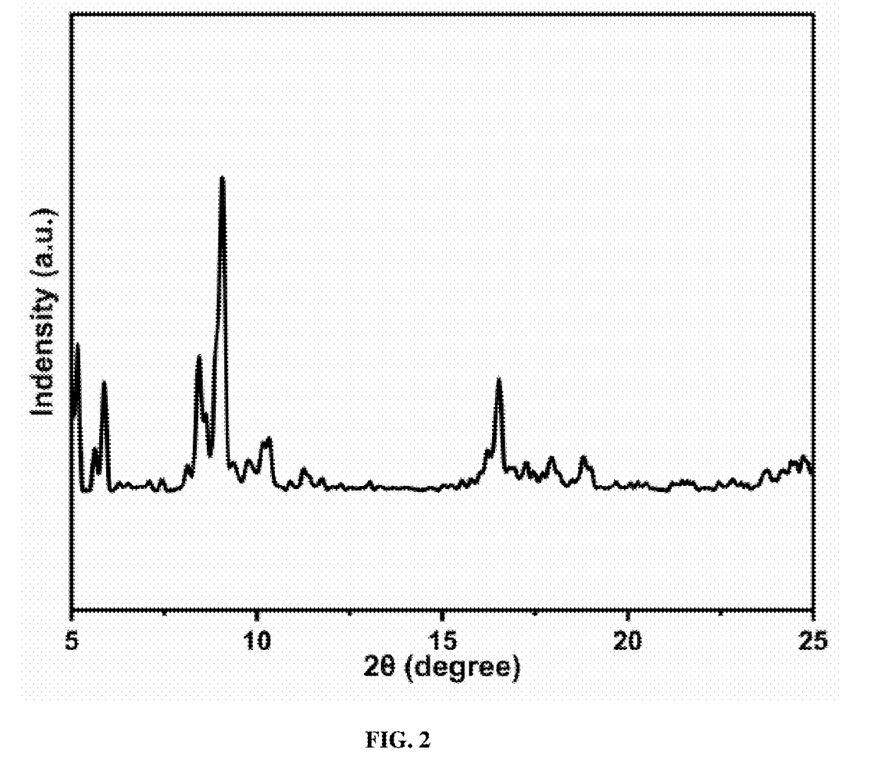
FIG. 2 is an X-ray diffraction spectrum diagram of a sample S1 prepared in Example 1.

In this example, the sulfo-containing metal organic framework catalyst is prepared by one-step synthesis, the preparation process is as follows: a metal precursor salt (10 g of zinc tetrachloride) and a ligand (11.6 g of 2-sulfoterephthalic acid) are dissolved in 800 mL of N,N-dimethylamide and fully stirred, and a mixture is poured into a crystallization kettle for static crystallization at 140° C. for 24 hours. An obtained crystallized product is filtered, washed with methanol and the N,N-dimethylamide, and dried, to obtain a sulfo-containing metal organic framework material S1. The obtained product S1 is subjected to XRD analysis, and an XRD spectrum is shown in FIG. 2, indicating that the product is the sulfo-containing metal organic framework catalyst with a structure. It can be shown from Table 1 that a specific surface area of the obtained sample S1 is 960 m2/g, a mean pore size is 4.5 nm, and sulfo content is 2.85 mmol/g.

In this example, the prepared sulfo-containing metal organic framework material S1 is put in the isomerization reactor, the catalyst S1 and the mother liquor are in contact in the fixed-bed reactor, a reaction temperature is 50° C., a reaction pressure is 0.1 MPaA, and a liquid hourly space velocity is preferably 0.1 $h^{-1}$. The sulfo-containing metal organic framework catalyst sample S1 obtained in Example 1 is used to catalyze the isomerization reaction of the mother liquor, a conversion rate of 2,4-BPA is 28%, and bisphenol A selectivity is 80%.

Example 2

In this example, a bisphenol A preparation process is the same as the bisphenol A preparation process in Example 1.

Figure 3:
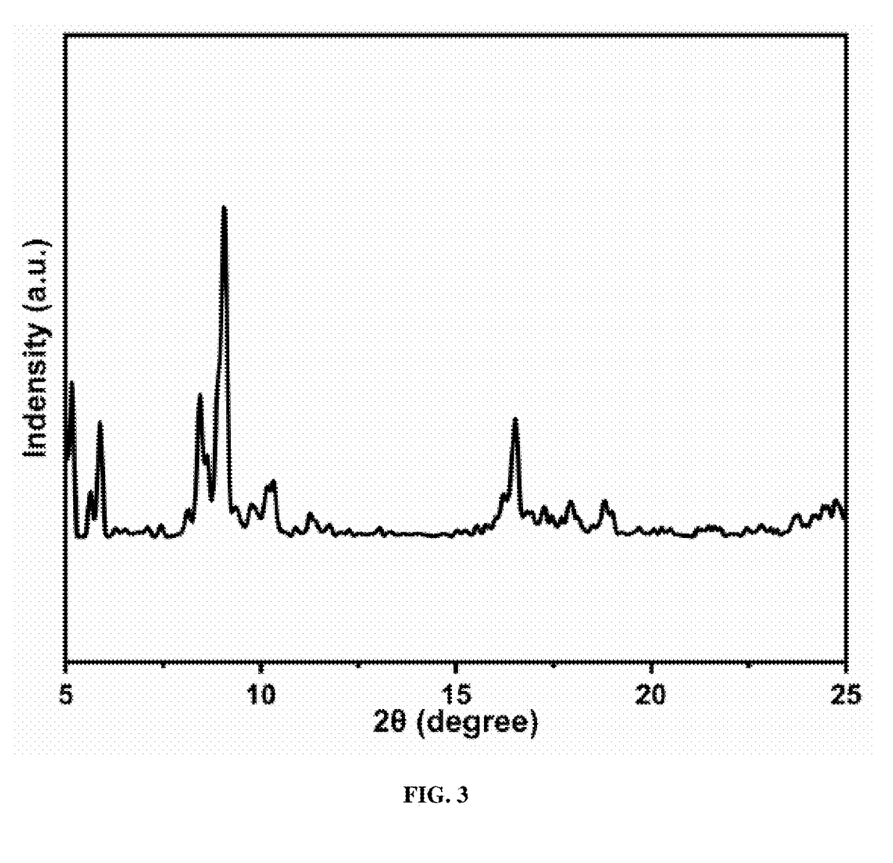
FIG. 3 is an X-ray diffraction spectrum diagram of a sample S2 prepared in Example 2.

In this example, the sulfo-containing metal organic framework catalyst is prepared by one-step synthesis, the preparation process is as follows: a metal precursor salt (10 g of hafnium chloride) and a ligand (7.4 g of 2,6-dicarboxyl-4,8-dinaphthalene sulfonic acid) are dissolved in 960 mL of N,N-dimethylamide and fully stirred, and a mixture is poured into a crystallization kettle for static crystallization at 160° C. for 36 hours. An obtained crystallized product is filtered, washed with ethanol, and dried, to obtain a sulfo-containing metal organic framework material S2. The obtained product S2 is subjected to XRD analysis, and an XRD spectrum is shown in FIG. 3, indicating that the product is the sulfo-containing metal organic framework catalyst with a structure. It can be shown from Table 1 that a specific surface area of the obtained sample S2 is 821 $m^2$/g, a mean pore size is 6.8 nm, and sulfo content is 3.46 mmol/g.

In this example, the prepared sulfo-containing metal organic framework material S2 is put in an isomerization reactor, the catalyst S2 and mother liquor are in contact in the fixed-bed reactor, a reaction temperature is 70° C., a reaction pressure is 0.2 MPaA, and a liquid hourly space velocity is preferably 10 $h^{-1}$. The sulfo-containing metal organic framework catalyst sample S2 obtained from Example 2 is used to catalyze the isomerization reaction of the mother liquor, a conversion rate of 2,4-BPA is 35%, and bisphenol A selectivity is 82%.

Example 3

In this example, a bisphenol A preparation process is the same as the bisphenol A preparation process in Example 1.

Figure 4:
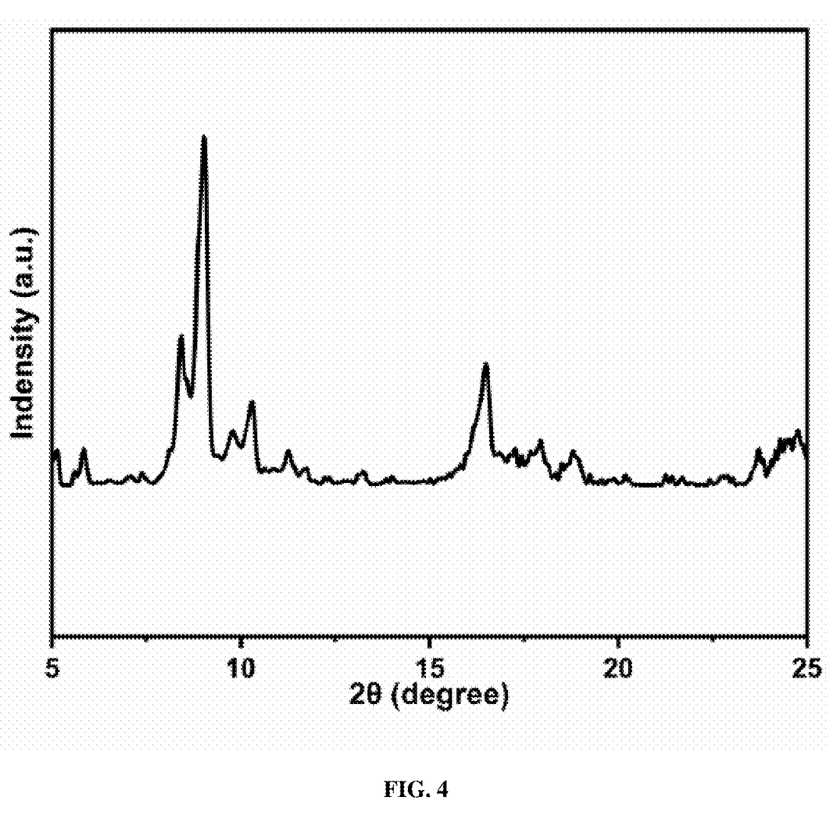
FIG. 4 is an X-ray diffraction spectrum diagram of a sample S3 prepared in Example 3.

In this example, the sulfo-containing metal organic framework catalyst is prepared by one-step synthesis, the preparation process is as follows: a metal precursor salt (10 g of aluminum nitrate) and a ligand (8.8 g of 1-sulfo trimesic acid) are dissolved in 780 mL of N,N-dimethylamide and fully stirred, and a mixture is poured into a crystallization kettle for static crystallization at 150° C. for 30 hours. An obtained crystallized product is filtered, washed with ethanol, and dried, to obtain a sulfo-containing metal organic framework material S3. The obtained product S3 is subjected to XRD analysis, and an XRD spectrum is shown in FIG. 4, indicating that the product is the sulfo-containing metal organic framework catalyst with a structure. It can be shown from Table 1 that a specific surface area of the obtained sample S3 is 803 $m^2$/g, a mean pore size is 6.5 nm, and sulfo content is 3.33 mmol/g.

In this example, the prepared sulfo-containing metal organic framework material S3 is put in an isomerization reactor, the catalyst S3 and mother liquor are in contact in the fixed-bed reactor, a reaction temperature is 65° C., a reaction pressure is 0.2 MPaA, and a liquid hourly space velocity is preferably 10 $h^{-1}$. The sulfo-containing metal organic framework catalyst sample S3 obtained from Example 3 is used to catalyze the isomerization reaction of the mother liquor, a conversion rate of 2,4-BPA is 39%, and bisphenol A selectivity is 84%.

Example 4

In this example, a bisphenol A preparation process is the same as the bisphenol A preparation process in Example 1.

Figure 5:
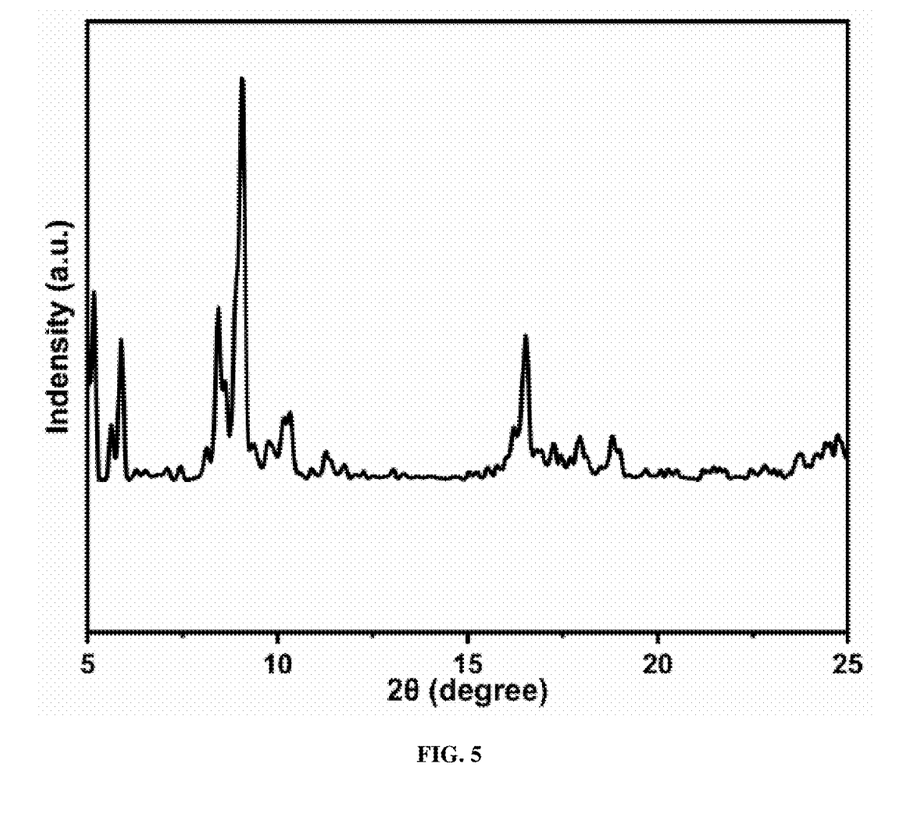
FIG. 5 is an X-ray diffraction spectrum diagram of a sample S4 prepared in Example 4.

In this example, the sulfo-containing metal organic framework catalyst is prepared by a post-synthesis acid treatment, the preparation process is as follows: a metal precursor salt (10.5 g of zirconium tetrachloride) and a ligand (10.5 g of terephthalic acid) are dissolved in 800 mL of N,N-dimethylamide and fully stirred, and a mixture is poured into a crystallization kettle for static crystallization at 120° C. for 24 hours. An obtained crystallized product is filtered, washed with the methanol and N,N-dimethylamide, and dried, to obtain a metal organic framework material. The obtained metal organic framework material is put in a polytetrafluoroethylene-lined reaction kettle, acid liquor (100 mL of chlorosulfonic acid) is added for sulfonation treatment at 100° C. for 24 hours, and an obtained product is filtered, washed, and dried, to obtain a sulfo-containing metal organic framework material S4. The obtained product S4 is subjected to XRD analysis, and an XRD spectrum is shown in FIG. 5, indicating that the product is the sulfo-containing metal organic framework catalyst with a structure. It can be shown from Table 1 that a specific surface area of the obtained sample S4 is 793 m$^2$/g, a mean pore size is 8.5 nm, and sulfo content is 5.57 mmol/g.

In this example, a bisphenol A preparation process is the same as the bisphenol A preparation process in Example 1.

In this example, the prepared sulfo-containing metal organic framework material S4 is put in an isomerization reactor, the catalyst S4 and mother liquor are in contact in the fixed-bed reactor, a reaction temperature is 90° C., a reaction pressure is 0.5 MPaA, and a liquid hourly space velocity is preferably 0.5 h$^{-1}$. The sulfo-containing metal organic framework catalyst sample S4 obtained in Example 4 is used to catalyze the isomerization reaction of the mother liquor, a conversion rate of 2,4-BPA is 37%, and bisphenol A selectivity is 90%.

Example 5

In this example, a bisphenol A preparation process is the same as the bisphenol A preparation process in Example 1.

Figure 6:
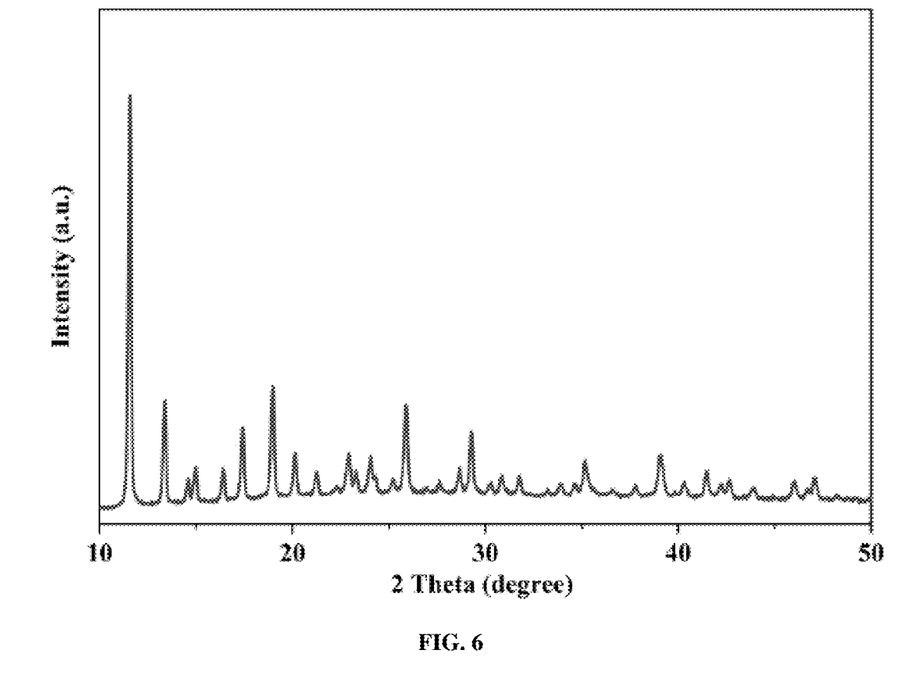
FIG. 6 is an X-ray diffraction spectrum diagram of a sample S5 prepared in Example 5.

In this example, the sulfo-containing metal organic framework catalyst is prepared by a post-synthesis acid treatment, the preparation process is as follows: a metal precursor salt (7.6 g of iron nitrate nonahydrate) and a ligand (6.5 g of trimesic acid) are dissolved in 700 mL of N,N-dimethylamide and fully stirred, and a mixture is poured into a crystallization kettle for static crystallization at 160° C. for 48 hours. An obtained crystallized product is filtered, washed with ethanol, and dried, to obtain a metal organic framework material. The obtained metal organic framework material is put in a polytetrafluoroethylene-lined reaction kettle, acid liquor (100 mL of 1,3-propanesultone) is added for sulfonation treatment at 180° C. for 24 hours, and an obtained product is filtered, washed, and dried, to obtain a sulfo-containing metal organic framework material S5. The obtained product S5 is subjected to XRD analysis, and an XRD spectrum is shown in FIG. 6, indicating that the product is the sulfo-containing metal organic framework catalyst with a structure. It can be shown from Table 1 that a specific surface area of the obtained sample S5 is 755 m$^2$/g, a mean pore size is 9.2 nm, and sulfo content is 4.22 mmol/g.

In this example, a bisphenol A preparation process is the same as the bisphenol A preparation process in Example 1.

In this example, the prepared sulfo-containing metal organic framework material S5 is put in an isomerization reactor, the catalyst S5 and mother liquor are in contact in the fixed-bed reactor, a reaction temperature is 60° C., a reaction pressure is 1.0 MPaA, and a liquid hourly space velocity is preferably 0.2 h$^{-1}$. The sulfo-containing metal organic framework catalyst sample S5 obtained in Example 5 is used to catalyze the isomerization reaction of the mother liquor, a conversion rate of 2,4-BPA is 43%, and bisphenol A selectivity is 90%.

Example 6

In this example, a bisphenol A preparation process is the same as the bisphenol A preparation process in Example 1.

Figure 7:
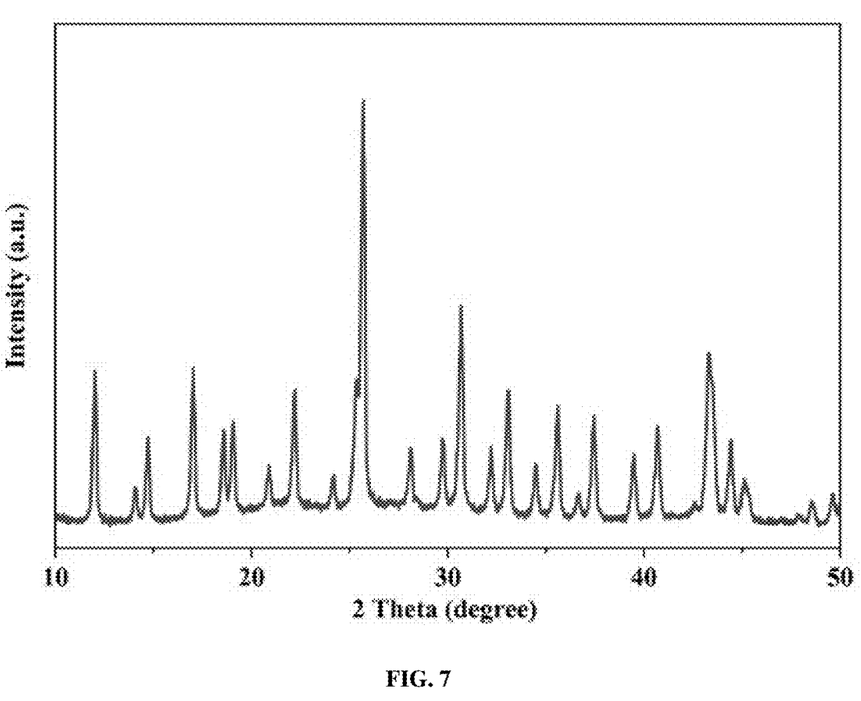
FIG. 7 is an X-ray diffraction spectrum diagram of a sample S6 prepared in Example 6.

In this example, the sulfo-containing metal organic framework catalyst is prepared by a post-synthesis acid treatment, the preparation process is as follows: a metal precursor salt (10 g of copper nitrate) and a ligand (6.5 g of trimesic acid) are dissolved in 700 mL of N,N-dimethylamide and fully stirred, and a mixture is poured into a crystallization kettle for static crystallization at 130° C. for 36 hours. An obtained crystallized product is filtered, washed with ethanol, and dried, to obtain a metal organic framework material. The obtained metal organic framework material is put in a polytetrafluoroethylene-lined reaction kettle, acid liquor (100 mL of 1,3-propanesultone) is added for sulfonation treatment at 180° C. for 24 hours, and an obtained product is filtered, washed, and dried, to obtain a sulfo-containing metal organic framework material S6. The obtained product S6 is subjected to XRD analysis, and an XRD spectrum is shown in FIG. 7, indicating that the product is the sulfo-containing metal organic framework catalyst with a structure. It can be shown from Table 1 that a specific surface area of the obtained sample S6 is 783 m$^2$/g, a mean pore size is 9.4 nm, and sulfo content is 4.36 mmol/g.

In this example, a bisphenol A preparation process is the same as the bisphenol A preparation process in Example 1.

In this example, the prepared sulfo-containing metal organic framework material S6 is put in an isomerization reactor, the catalyst S6 and mother liquor are in contact in the fixed-bed reactor, a reaction temperature is 65° C., a reaction pressure is 1.0 MPaA, and a liquid hourly space velocity is preferably 0.2 h$^{-1}$. The sulfo-containing metal organic framework catalyst sample S6 obtained in Example 6 is used to catalyze the isomerization reaction of the mother liquor, a conversion rate of 2,4-BPA is 47%, and bisphenol A selectivity is 88%.

Example 7

In this example, a bisphenol A preparation process is the same as the bisphenol A preparation process in Example 1.

Figure 8:
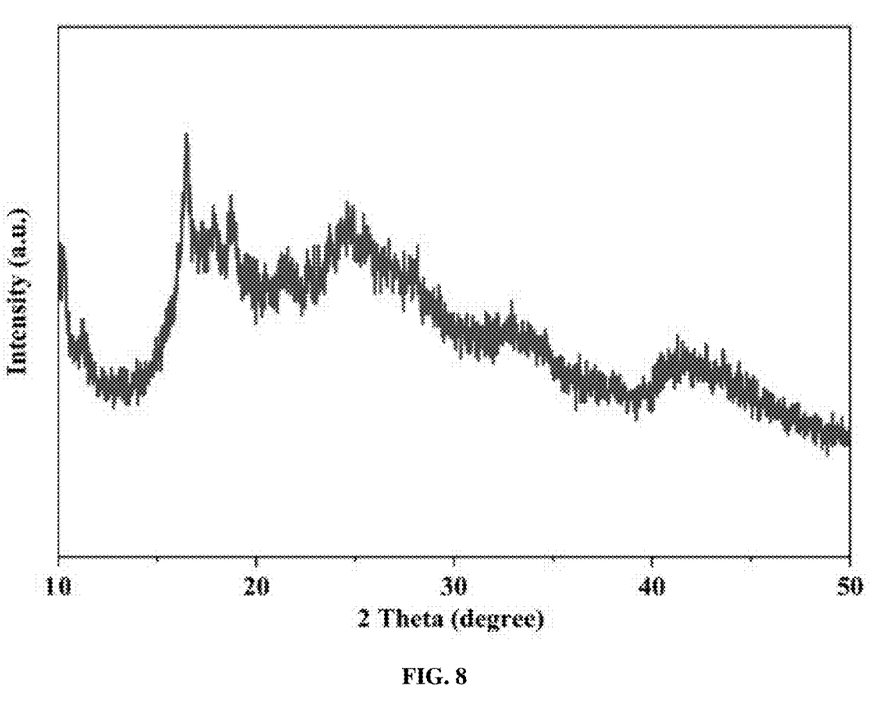
FIG. 8 is an X-ray diffraction spectrum diagram of a sample S7 prepared in Example 7.

In this example, the sulfo-containing metal organic framework catalyst is prepared by a post-synthesis oxidation treatment, the preparation process is as follows: a metal precursor salt (10 g of chromium nitrate) and a ligand (8.3 g of 2,5-dimercaptoterephthalic acid) are dissolved in 660 mL of N,N-dimethylamide and fully stirred, and a mixture is poured into a crystallization kettle for static crystallization at 110° C. for 24 hours. An obtained crystallized product is filtered, washed with ethanol, and dried, to obtain a metal organic framework material. The obtained metal organic framework material is put in a polytetrafluoroethylene-lined reaction kettle, oxidative liquor (20 mL of hydrogen peroxide) is added for oxidation treatment at 50° C. for 2 hours, and an obtained product is filtered, washed, and dried, to obtain a sulfo-containing metal organic framework material S7. The obtained product S7 is subjected to XRD analysis, and an XRD spectrum is shown in FIG. 8, indicating that the product is the sulfo-containing metal organic framework catalyst with a structure. It can be shown from Table 1 that a specific surface area of the obtained sample S7 is 726 m$^2$/g, a mean pore size is 10.5 nm, and sulfo content is 6.02 mmol/g.

In this example, a bisphenol A preparation process is the same as the bisphenol A preparation process in Example 1.

In this example, the prepared sulfo-containing metal organic framework material S7 is put in an isomerization reactor, the catalyst S7 and mother liquor are in contact in the fixed-bed reactor, a reaction temperature is 80° C., a reaction pressure is 0.7 MPaA, and a liquid hourly space velocity is preferably 3.0 h$^{-1}$. The sulfo-containing metal organic framework catalyst sample S7 obtained from Example 7 is used to catalyze the isomerization reaction of the mother liquor, a conversion rate of 2,4-BPA is 55%, and bisphenol A selectivity is 87%.

Example 8

In this example, a bisphenol A preparation process is the same as the bisphenol A preparation process in Example 1.

Figure 9:
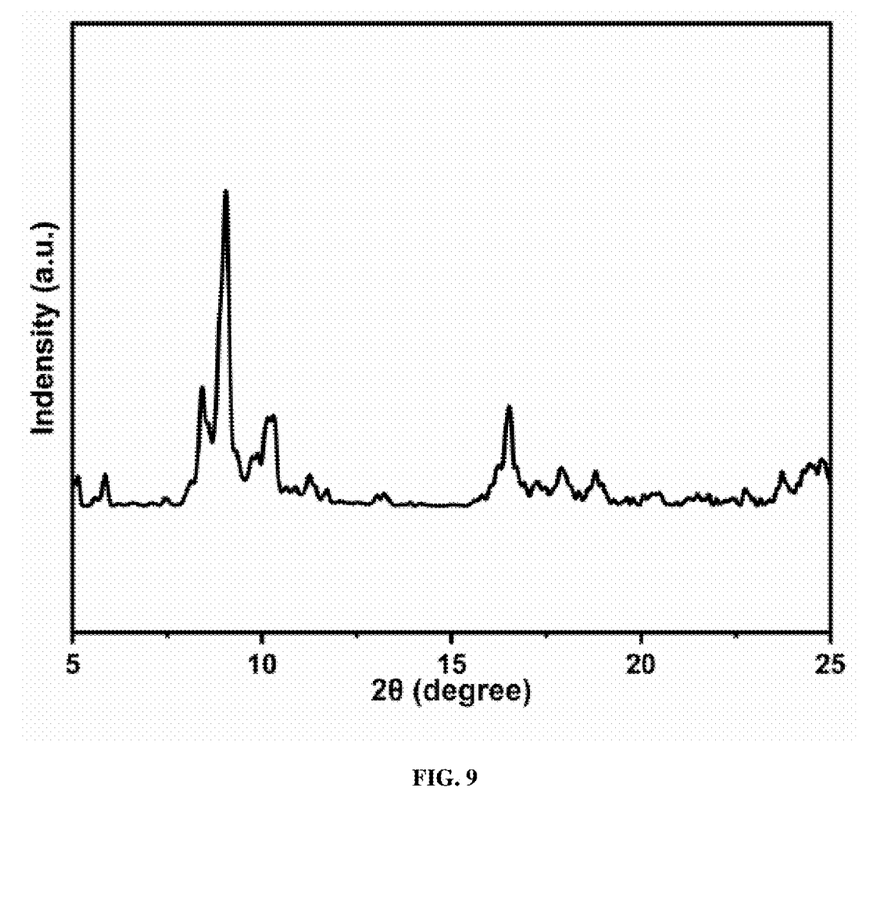
FIG. 9 is an X-ray diffraction spectrum diagram of a sample S8 prepared in Example 8.

In this example, the sulfo-containing metal organic framework catalyst is prepared by a post-synthesis oxidation, the preparation process is as follows: a metal precursor salt (10 g of titanium chloride) and a ligand (7.4 g of 4,8-dimercapto-2,6-naphthalenedicarboxylic acid) are dissolved in 850 mL of N,N-dimethylamide and fully stirred, and a mixture is poured into a crystallization kettle for static crystallization at 140° C. for 48 hours. An obtained crystallized product is filtered, washed with ethanol, and dried, to obtain a metal organic framework material. The obtained metal organic framework material is put in a polytetrafluoroethylene-lined reaction kettle, oxidative liquor (35 mL of hydrogen peroxide) is added for oxidation treatment at 60° C. for 6 hours, and an obtained product is filtered, washed, and dried, to obtain a sulfo-containing metal organic framework material S8. The obtained product S8 is subjected to XRD analysis, and an XRD spectrum is shown in FIG. 9, indicating that the product is the sulfo-containing metal organic framework catalyst with a structure. It can be shown from Table 1 that a specific surface area of the obtained sample S8 is 866 m$^2$/g, a mean pore size is 5.7 nm, and sulfo content is 4.38 mmol/g.

In this example, a bisphenol A preparation process is the same as the bisphenol A preparation process in Example 1.

In this example, the prepared sulfo-containing metal organic framework material S8 is put in an isomerization reactor, the catalyst S8 and mother liquor are in contact in the fixed-bed reactor, a reaction temperature is 70° C., a reaction pressure is 0.5 MPaA, and a liquid hourly space velocity is preferably 7.0 h$^{-1}$. The sulfo-containing metal organic framework catalyst sample S8 obtained in Example 8 is used to catalyze the isomerization reaction of the mother liquor, a conversion rate of 2,4-BPA is 48%, and bisphenol A selectivity is 89%.

Example 9

In this example, a bisphenol A preparation process is the same as the bisphenol A preparation process in Example 1.

Figure 10:
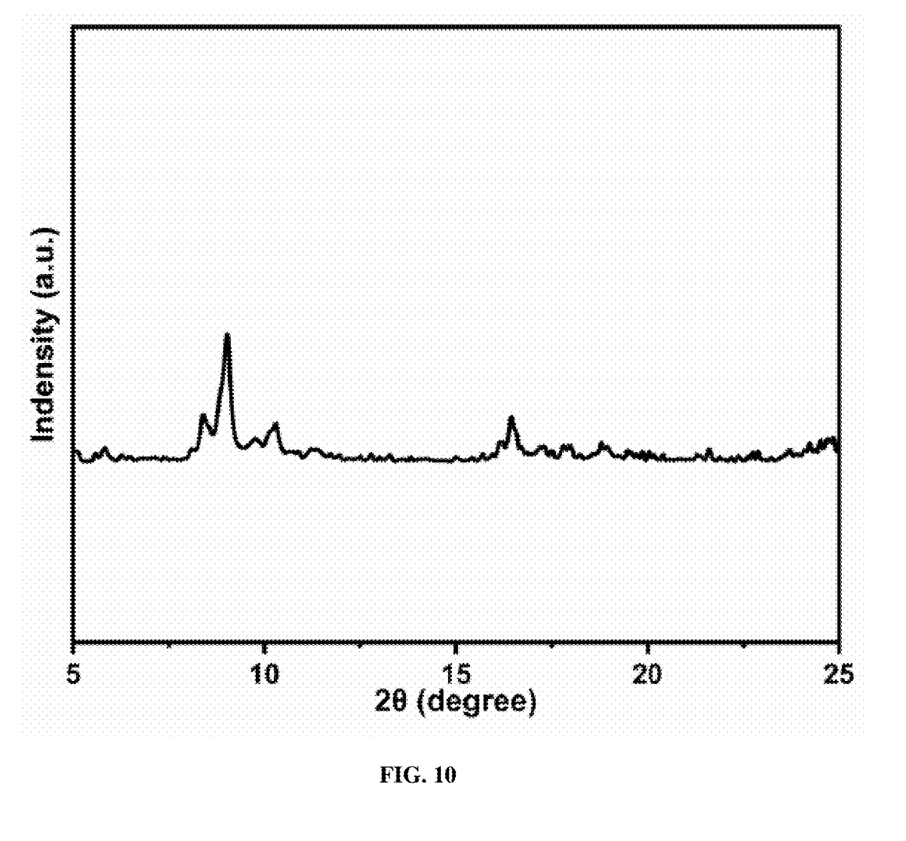
FIG. 10 is an X-ray diffraction spectrum diagram of a sample S9 prepared in Example 9.

In this example, the sulfo-containing metal organic framework catalyst is prepared by a post-synthesis oxidation preparation process of a is as follows: a metal precursor salt (6.6 g of magnesium nitrate and 3.4 g cerium nitrate) and a ligand (6.9 g of 2,5-dimercaptoterephthalic acid) are dissolved in 820 mL of N,N-dimethylamide and fully stirred, and a mixture is poured into a crystallization kettle for static crystallization at 120° C. for 36 hours. An obtained crystallized product is filtered, washed with ethanol, and dried, to obtain a metal organic framework material. The obtained metal organic framework material is put in a polytetrafluoroethylene-lined reaction kettle, oxidative liquor (40 mL of hydrogen peroxide) is added for oxidation treatment at 55° C. for 4 hours, and an obtained product is filtered, washed, and dried, to obtain a sulfo-containing metal organic framework material S9. The obtained product S9 is subjected to XRD analysis, and an XRD spectrum is shown in FIG. 10, indicating that the product is the sulfo-containing metal organic framework catalyst with a structure. It can be shown from Table 1 that a specific surface area of the obtained sample S9 is 833 m$^2$/g, a mean pore size is 5.3 nm, and sulfo content is 4.06 mmol/g.

In this example, a bisphenol A preparation process is the same as the bisphenol A preparation process in Example 1.

In this example, the prepared sulfo-containing metal organic framework material S9 is put in an isomerization reactor, the catalyst S9 and mother liquor are in contact in the fixed-bed reactor, a reaction temperature is 65° C., a reaction pressure is 0.5 MPaA, and a liquid hourly space velocity is preferably 6.0 h$^{-1}$. The sulfo-containing metal organic framework catalyst sample S9 obtained from Example 9 is used to catalyze an isomerization reaction of the mother liquor, a conversion rate of 2,4-BPA is 45%, and bisphenol A selectivity is 87%.

In the above examples, calculation methods for the conversion rate of 2,4-BPA and bisphenol A selectivity are as follows:

Conversion rate of 2,4-BPA=(feed quantity of 2,4-BPA−quantity of unreacted 2,4-BPA)/feed quantity of 2,4-BPA×100%.

Bisphenol A selectivity=yield of bisphenol A/quantity of products produced from 2,4-BPA×100%.

In the method provided by the patent for the present disclosure, the method for converting 2,4-BPA into bisphenol A by isomerization of a mixture containing 2,4-BPA, phenol and the bisphenol A adduct as a raw material is proposed for the by-product 2,4-BPA in production of bisphenol A. In order to show an effect of the catalyst in catalytically converting 2,4-BPA into bisphenol A in the method provided by the patent for the present disclosure, 2,4-BPA is used as the raw material for the isomerization reaction in Example 1 to Example 9, and obtained results are shown in Table 2. It can be shown from Table 2 that the sulfo-containing metal organic framework catalyst samples S1 to S9 obtained in Example 1 to Example 9 have a good conversion rate of 2,4-BPA (28% to 55%), and bisphenol A selectivity in the sulfo-containing metal organic framework catalysts is high (80% to 90%). This means that the purpose of catalyzing the efficient isomerization of 2,4-BPA to prepare bisphenol A is achieved by utilizing the sulfo-containing metal organic framework catalyst in the patent for the present disclosure. In view of the effect of catalyzing, by the catalyst, the isomerization reaction of 2,4-BPA to produce bisphenol A, the method provided by the patent for the present disclosure can catalytically convert the by-product 2,4-BPA in bisphenol A, content of the by-product 2,4-BPA can be significantly reduced, and 2,4-BPA can be converted into bisphenol A with high selectivity. In conclusion, it can be shown that by the adoption of the method provided by the patent for the present disclosure, the quantity of the by-product 2,4-BPA in production of bisphenol A can be significantly reduced, and meanwhile 2,4-BPA is converted into bisphenol A with high selectivity, thereby increasing the yield of bisphenol A.

TABLE 1

| Sample | Metal composition | Specific surface area (m$^2$/g) | Mean pore size (nm) | Sulfo content (mmol/g) |
| --- | --- | --- | --- | --- |
| S1 in Example 1 | Zn | 960 | 4.5 | 2.85 |
| S2 in Example 2 | Hf | 821 | 6.8 | 3.46 |
| S3 in Example 3 | Al | 803 | 6.5 | 3.33 |
| S4 in Example 4 | Zr | 793 | 8.5 | 5.57 |

TABLE 1-continued

| Sample | Metal composition | Specific surface area (m²/g) | Mean pore size (nm) | Sulfo content (mmol/g) |
|---|---|---|---|---|
| S5 in Example 5 | Fe | 755 | 9.2 | 4.22 |
| S6 in Example 6 | Cu | 783 | 9.4 | 4.36 |
| S7 in Example 7 | Cr | 726 | 10.5 | 6.02 |
| S8 in Example 8 | Ti | 866 | 5.7 | 4.38 |
| S9 in Example 9 | Mg and Ce | 833 | 5.3 | 4.06 |

TABLE 2

| Sample | Conversion rate of 2,4-BPA (%) | Bisphenol A selectivity (%) |
|---|---|---|
| S1 in Example 1 | 28 | 80 |
| S2 in Example 2 | 35 | 82 |
| S3 in Example 3 | 39 | 84 |
| S4 in Example 4 | 37 | 90 |
| S5 in Example 5 | 43 | 90 |
| S6 in Example 6 | 47 | 88 |
| S7 in Example 7 | 55 | 87 |
| S8 in Example 8 | 48 | 89 |
| S9 in Example 9 | 45 | 87 |

The foregoing details of preferred implementations of the present disclosure have been described in conjunction with the accompanying drawings, however, the present disclosure is not limited to the specific details of the foregoing implementations, and various simple modifications may be made to the technical solution of the present disclosure within the scope of the technical concept of the present disclosure, where all the simple modifications fall within the scope of protection of the present disclosure.

In addition, it should be noted that various specific technical features described in the foregoing specific implementations can be combined in any appropriate manner without conflicts, and in order to avoid unnecessary repetitions, various possible combination manners are not additionally specified in the present disclosure.

In addition, various different implementations of the present disclosure can also be combined at will, and should also be regarded as the content disclosed in the present disclosure without departing from the thought of the present disclosure.

What is claimed is:

1. A process for reducing by-products in a bisphenol A reaction system, comprising the following steps:
   (a) conveying mother liquor to a mother liquor recovery system, wherein the mother liquor is produced by reaction, concentration, crystallization and separation of phenol and acetone;
   (b) subjecting the mother liquor obtained from the mother liquor recovery system to contact with a sulfo-containing metal organic framework catalyst for an isomerization reaction; and
   (c) conveying a product obtained from the isomerization reaction to the mother liquor recovery system, performing crystallization and dephenolization to obtain bisphenol A;
   wherein the sulfo-containing metal organic framework catalyst in step (b) is formed by connecting metal ions or metal clusters and organic ligands through coordination bonds, and metal contained therein is one or a combination of Al, Mg, Ti, Cr, Fe, Cu, Zn, Zr, Ce, and Hf; the organic ligands are one or a combination of terephthalic acid and trimesic acid; a pore size of the catalyst ranges from 0.5 nm to 10 nm, a specific surface area ranges from 100 m²/g to 5,000 m²/g, and an amount of sulfo groups ranges from 0.01 mmol/g to 8.0 mmol/g;
   the sulfo-containing metal organic framework catalyst is prepared by any one of a one-step synthesis preparation method, postsynthesis acid treatment preparation method, or postsynthesis oxidation treatment preparation method;
   the one-step synthesis preparation method of the sulfo-containing metal organic framework catalyst comprises the following steps: dissolving and stirring metal precursor salts and sulfo-containing organic ligands in N,N-dimethylamide and then static crystallizing the solution in a crystallization kettle at 140° C. to 160° C. for 24 hours to 36 hours, and subjecting an obtained crystallized product to filtering, washing with methanol and the N,N-dimethylamide, and drying, to obtain a sulfo-containing metal organic framework material; wherein the metal precursor salt is one or a combination of oxides, nitrates, chloride salts, and acetylacetonates of one or a combination of Al, Mg, Ti, Cr, Fe, Cu, Zn, Zr, Ce, and Hf; the sulfo-containing organic ligands are one or a combination of benzoic acid with sulfo groups, terephthalic acid with sulfo groups, and trimesic acid with sulfo groups;
   the post-synthesis acid treatment preparation method of the sulfo-containing metal organic framework catalyst comprises the following steps: dissolving and stirring metal precursor salts and organic ligands in N,N-dimethylamide and then static crystallizing the solution in a crystallization kettle at 120° C. to 160° C. for 24 hours to 48 hours, and subjecting a crystallized product obtained in the crystallization kettle to filtering, washing with methanol and the N,N-dimethylamide, and drying, to obtain a metal organic framework precursor; and putting the obtained metal organic framework precursor into a polytetrafluoroethylene-lined reaction kettle, adding acidic liquor, sulfonating at 100° C. to 180° C. for 24 hours, and subjecting an obtained product to filtering, washing, and drying, to obtain a sulfo-containing metal organic framework material; wherein the metal precursor salt is one or a combination of oxides, nitrates, chloride salts, and acetylacetonates of one or a combination of Al, Mg, Ti, Cr, Fe, Cu, Zn, Zr, Ce, and Hf; the organic ligands are one or a combination of terephthalic acid not containing amino groups or containing amino groups and trimesic acid not containing amino groups or containing amino groups; the metal organic framework precursor is formed by connecting metal ions or metal clusters and organic ligands through coordination bonds; and the acidic liquor is one or a combination of sulfuric acid, chlorosulfonic acid, and 1,3-propanesultone; and
   the post-synthesis oxidation treatment preparation method of the sulfo-containing metal organic framework catalyst comprises the following steps: dissolving and stirring metal precursor salts and sulfydryl-containing organic ligands in N,N-dimethylamide and then static crystallizing the solution in a crystallization kettle at 110° C. to 140° C. for 24 hours to 48 hours, and subjecting a crystallized product obtained in the crystallization kettle to filtering, washing with ethanol, and drying, to obtain a metal organic framework precursor; and putting the obtained metal organic framework precursor into a polytetrafluoroethylene-lined reaction kettle, adding oxidative liquor, oxidizing at 50° C. to 60° C. for 2 hours to 6 hours, and subjecting an obtained product to filtering, washing, and drying, to obtain a sulfo-containing metal organic framework material; wherein the metal precursor salt is one or a combination of oxides, nitrates, chloride salts, and acetylacetonates of one or a combination of Al, Mg, Ti, Cr, Fe, Cu, Zn, Zr, Ce, and Hf; the organic ligands are one or more combinations of terephthalic acid containing alkyl sulfydryl or amino sulfydryl and trimesic acid containing alkyl sulfydryl or amino sulfydryl; the metal organic framework precursor is formed by connecting metal ions or metal clusters and organic ligands through coordination bonds; the oxidative liquor is hydrogen peroxide.

2. The process for reducing the by-products in the bisphenol A reaction system according to claim 1, wherein the step (a) comprises: the phenol and the acetone are synthesized in a bisphenol A reactor (101), to obtain bisphenol A, and bisphenol A reaction liquor from an outlet of the bisphenol A reactor (101) is conveyed to a concentration tower (102) for concentration; light components obtained from a tower top of the concentration tower (102) are recovered by a solvent recovery system, to obtain the phenol and the acetone, and the phenol and the acetone are conveyed to the bisphenol A reactor (101); concentrated reaction liquor obtained from a tower kettle of the concentration tower (102) is conveyed to a crystallization reactor (103) for crystallization with the phenol, to obtain a bisphenol A adduct and reactor crystallization mother liquor; the bisphenol A adduct is conveyed to a dephenolization reactor (104) to remove the phenol therefrom, to obtain a bisphenol A product, the removed phenol is conveyed to the mother liquor recovery system (106); the reactor crystallization mother liquor is conveyed to the mother liquor recovery system (106) for mother liquor recovery; and the phenol recovered from the mother liquor recovery system (106) is conveyed to the bisphenol A reactor (101), and the bisphenol A adduct recovered from the mother liquor recovery system (106) is conveyed to the crystallization reactor (103).

3. The process for reducing the by-products in the bisphenol A reaction system according to claim 1, wherein the step (b) comprises: one part of recovery system crystallization mother liquor obtained after recovery of the phenol and the bisphenol A adduct from the mother liquor recovery system (106) is conveyed to an isomerization reactor (107) filled with the sulfo-containing metal organic framework catalyst for an isomerization reaction; the other part of the recovery system crystallization mother liquor is conveyed to a cracking rearrangement reactor (108) for a cracking rearrangement reaction, and an obtained cracking rearrangement product is conveyed to the mother liquor recovery system (106); wherein, in the isomerization reaction, the catalyst is contacted with the mother liquor in a fixed-bed reaction, the reaction temperature ranging from 50° C. to 90° C., a reaction pressure ranging from 0.1 MPaA to 1.0 MPaA, and a liquid hourly space velocity ranging from 0.1 $h^{-1}$ to 10 $h^{-1}$.

4. The process for reducing the by-products in the bisphenol A reaction system according to claim 1, wherein the step (c) comprises: an isomerization product from an outlet of the isomerization reactor (107) is conveyed to the mother liquor recovery system (106) for crystallization with the phenol through the crystallization reactor (103), to obtain the bisphenol A adduct, and the bisphenol A adduct enters the dephenolization reactor (104) to remove the phenol therefrom, to obtain the bisphenol A product.

5. The process for reducing the by-products in the bisphenol A reaction system according to claim 2, wherein the recovery system crystallization mother liquor in the step (a) is a mixture containing 2,4-BPA, the phenol, and the bisphenol A adduct; and the isomerization reactor is a fixed-bed reactor.

* * * * *